(12) United States Patent
Carriere Lluch

(10) Patent No.: US 9,987,104 B2
(45) Date of Patent: *Jun. 5, 2018

(54) ORTHODONTIC LINGUAL DEVICE

(71) Applicant: ORTHODONTIC RESEARCH AND DEVELOPMENT, S.L., Barcelona (ES)

(72) Inventor: Luis Carriere Lluch, Barcelona (ES)

(73) Assignee: ORTHODONTIC RESEARCH AND DEVELOPMENT, S.L., Barcelona (ES)

(*) Notice: Subject to any disclaimer, the term of this patent is extended or adjusted under 35 U.S.C. 154(b) by 0 days. days.

This patent is subject to a terminal disclaimer.

(21) Appl. No.: 15/482,484

(22) Filed: Apr. 7, 2017

(65) Prior Publication Data
US 2017/0209240 A1    Jul. 27, 2017

Related U.S. Application Data

(63) Continuation of application No. 14/743,323, filed on Jun. 18, 2015, now Pat. No. 9,649,176.

(30) Foreign Application Priority Data

Jun. 20, 2014 (EP) .................................... 14382242

(51) Int. Cl.
 *A61C 7/14* (2006.01)
 *A61C 7/36* (2006.01)
 (Continued)

(52) U.S. Cl.
 CPC ................ *A61C 7/145* (2013.01); *A61C 7/00* (2013.01); *A61C 7/12* (2013.01); *A61C 7/14* (2013.01); *A61C 7/36* (2013.01)

(58) Field of Classification Search
 None
 See application file for complete search history.

(56) References Cited

U.S. PATENT DOCUMENTS

| 7,238,022 B2 | 7/2007 | Lluch |
| 2003/0157455 A1 | 8/2003 | Teramoto |

(Continued)

FOREIGN PATENT DOCUMENTS

| DE | 19751735 C1 | 5/1999 |
| EP | 1649824 A1 | 4/2006 |

(Continued)

OTHER PUBLICATIONS

European Search Report for EP14382242.7 dated Dec. 22, 2014, 9 pages.

*Primary Examiner* — Brian T Gedeon
(74) *Attorney, Agent, or Firm* — Squire Patton Boggs (US) LLP

(57) ABSTRACT

Orthodontic devices for segmental distalization in a patient are provided. The orthodontic device includes an elongated central arm; a distal part comprising a distal base surface adapted for attachment to a lingual surface of a molar, wherein the distal part is located at a distal end of the central arm. The device also includes a mesial part comprising a mesial base surface adapted for attachment to a lingual surface of a premolar, wherein the mesial part is located at a mesial end of the central arm. The mesial part and/or distal part comprising a first retention element for retention of a first end of an elastic element. The central arm is shaped to substantially follow a lingual side of a set of teeth. The present disclosure further relates to orthodontic kits and to methods for mounting orthodontic devices and to methods for treatment of malocclusions.

13 Claims, 9 Drawing Sheets

(51) Int. Cl.
*A61C 7/00* (2006.01)
*A61C 7/12* (2006.01)

(56) References Cited

U.S. PATENT DOCUMENTS

2007/0218415 A1 9/2007 Lluch
2011/0244414 A1 10/2011 Lluch

FOREIGN PATENT DOCUMENTS

EP          1681033 A1   7/2006
WO   WO 2009/150634 A2  12/2009

ORTHODONTIC LINGUAL DEVICE

This application claims priority to European Application No. 14382242.7, filed Jun. 20, 2014, the disclosure of which is hereby incorporated by reference in its entirety.

The present disclosure relates to an orthodontic device, and more particularly relates to an orthodontic lingual device for segmental distalization. The present disclosure further relates to methods for mounting and using orthodontic devices.

BACKGROUND ART

The correction of dental irregularities and malocclusions by applying controlled forces to the teeth has become commonplace. One of the most important aims for orthodontics is to arrange space for teeth in the jaw in such a manner that the teeth can be positioned properly and they can contact each other in their desired positions.

Several methods and mechanisms for orthodontic treatments are known in order to correct the misalignment of teeth or incorrect relations between teeth. Some of the mechanisms that are typically employed include e.g. headgear. In these systems, an orthodontic bracket fitted to the upper molar brace is provided with a head gear tube. The head gear wire is inserted into the head gear tube and tensile forces are exerted on the head gear wire by a strap extending behind a patient's neck.

However, one drawback of these solutions may be the unpleasant design that makes the orthodontic treatment easily noticeable in the mouth, furthermore, an unpleasant feeling may be experimented with these very invasive solutions. Some other problem may be that the quality of the speech may be affected.

It is also problematic that such devices may be poking the lips and/or cheeks continuously and a discomfort in the mouth may be caused.

A distalizing element is known from e.g. EP1649824. This document relates to an auxiliary element for the segmental distalization of the canine-to-molar posterior maxillary area in orthodontic treatments. Many of the aforementioned problems are at least partially resolved by such a distalizing element.

Segmental or segmented distalization herein is to be understood as distalization of a group of teeth exclusively in either the right mandible or left mandible, right maxilla or left maxilla.

For some patients however, other solutions are desirable.

SUMMARY

In a first aspect, an orthodontic device for segmental distalization in a patient is provided. The orthodontic device includes an elongated central arm; a distal part comprising a distal base surface adapted to be attached to a lingual surface of a molar, wherein the distal part is located at a distal end of the elongated central arm. The device also includes a mesial part comprising a mesial base surface adapted to be attached to a lingual surface of a premolar, wherein the mesial part is located at a mesial end of the elongated central arm. The mesial part and/or the distal part comprises a first retention element for retention of a first end of an external actuating element. The elongated central arm is shaped to substantially follow a lingual side of a set of teeth between the molar and the premolar of the patient.

The mesial part may comprise a first hooking element for retention of a first end of an elastic element e.g. a rubber band that may be suspended around the hook. Consequently, a force pulling the premolar backwards (mesial-distal direction) may be provided. Alternatively, or additionally, the distal part may comprise a first retention element e.g. a pocket for receiving a first end of an (elastic) piston. In this case, the distal part can be pushed backwards. The actuating element may be external to the device.

Due to the elongated central arm connecting the distal part and the mesial part, a molar may be pushed or pulled backwards. The central arm (or "central bar") connects the distal part of the device to the mesial part. At the same time, due to the position of the distal base surface onto a lingual surface of the molar, a rotational force in a pivot about the root(s) of a molar may be provided. Furthermore, a rotation in the distal direction of a molar ("uprighting") may be achieved.

The rotational force pivoting the molar around its root(s) could be expected to have a negative effect on the position of the molar in that the rotation of the molar is contrary to the desired result. It has however been found that due to the fact that the distalization is segmental (i.e. involves a block of teeth) and due to the point of contact between the teeth, the teeth located mesial of the molar bring about a moment that compensates the undesired moment brought about by the attachment of the device on the lingual side of the molar.

Contrary to prior art segmental distalization devices, the orthodontic device according to this aspect is adapted to be attached to a premolar instead of a canine. The number of teeth to be displaced is thus smaller than in such a prior art device. The elongated central arm may thus be shorter and straighter, which can result in an improved efficiency of device. As less transceptal fibres of periodontal tissue are included, the efficiency may be improved.

It has thus been found that an orthodontic device may be mounted onto the lingual surfaces of a molar and a premolar. In this way, the orthodontic device may be aesthetically pleasant, by ensuring that the orthodontic device is hardly observable in the mouth The provision of a distalizing element on a lingual side of the teeth furthermore provides additional and/or improved anchoring methods as compared to the prior art. For example, the palate, and in particular the hard palate provides a relatively large area for implanting anchors such as TAD's, mini-implants or mini-screws (bone anchorage). Anchors in the hard palate do not interfere with roots of teeth while the teeth themselves may be subject to moving as a result of the treatment. The provision of the device on the lingual side thus enables and enhances intra-maxillary traction (pushing or pulling between anchor and orthodontic device) instead of inter-maxillary traction.

The elongated central arm of the orthodontic device may be adapted e.g. curved in order to follow the lingual side of different sets of teeth e.g. between a molar and a premolar of the patient. The central arm thus does not have to interfere with the tongue. The central arm may be slightly concave when seen from the inside of the mouth. The orthodontic device may thus be used in different parts of the mouth e.g. the left quadrant of the mandible, the right quadrant of the mandible, the left quadrant of the maxilla, the right quadrant of the maxilla, thus the flexibility and the usability of the device may be improved as compared to prior art devices.

Furthermore, the orthodontic device may be adapted to be fitted between a first premolar, and a first molar, or a second molar or a third molar ("wisdom tooth"). The orthodontic device can also be adapted to fit between a second premolar, and a first molar, or a second molar or a third molar. A trained professional may choose from these options in accordance with a patient's malocclusion.

In some examples, the distal part of the elongated central arm may be provided with flexibility such that an angle between the distal part of the elongated central arm and a neighbouring portion of the elongated central arm can be adapted. In this way, the orthodontic device may be elastically deformed in the distal part; due to this pre-deformation the orthodontic device may be installed with an initial tension, thus an extra force may be exerted on a molar in a lingual direction ("inwards"). This can provide for a counterclockwise rotation of a molar in a right quadrant (when seen from above) or a clockwise rotation of a molar in a left quadrant. This rotation is generally desirable in many patients to fully correct their malocclusions.

In another aspect, a kit is provided further comprising an anchor including a second retention element for retention of a second end of the actuating element. A patient may be provided with an anchor device e.g. a splint, a bracket, an implant (or another anchor device) that may act as a solid fixation device to retain the another end of the actuating element.

In yet another aspect, a method for mounting a device substantially as hereinbefore described is provided. The method for mounting includes elastically deforming a distal end region of the central elongated arm, and mounting said at least one end to a tooth, such that the device is pre-stressed when mounted.

In a further aspect, a method for treating a malocclusion in a patient is provided. The method may comprise mounting a lingual orthodontic device substantially as hereinbefore described on a premolar and a molar. The method may furthermore comprise attaching an actuating element to a retention element on the lingual orthodontic device. The method may furthermore comprise monitoring the movement of a set of teeth of the mandible with respect to the maxilla (or the other way round) and removing the orthodontic device when the mandibular teeth and maxillary teeth in a posterior section of the mouth are aligned. Subsequently, brackets may be provided.

Optionally, the backwards force provided during treatment of the malocclusion may be varied by e.g. changing the stiffness of the actuating element. For example, if the actuating element is a rubber band, throughout the treatment such a rubber band can be substituted by another rubber band of different stiffness and elasticity.

In some examples, such a method for treatment may comprise elastically deforming a distal portion of the orthodontic device and monitoring the orientation of the molar. Optionally, the inwards force applied by the distal portion to the molar may be varied throughout the treatment.

BRIEF DESCRIPTION OF THE DRAWINGS

Non-limiting examples of the present disclosure will be described in the following, with reference to the appended drawings, in which.

DETAILED DESCRIPTION OF EXAMPLES

Figure 1:
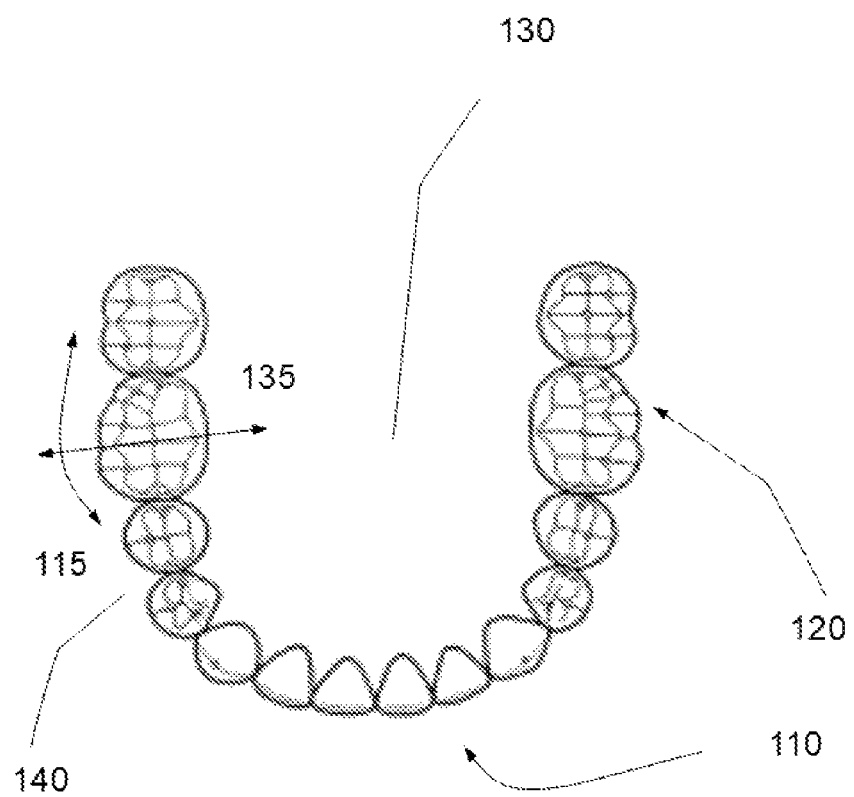
FIG. 1 illustrates some of the terminology used herein.

FIG. 1 illustrates the configuration of the teeth in the mandible (lower jaw bone). A rear part of the mouth 120 may be referred to as a distal part of the mouth. A front part of the mouth 110 may be referred to as a mesial part of the mouth. An inner portion of the mouth behind the teeth 130 may be referred to as a lingual region. An outer portion of the mouth 140 may be referred to as a labial region. A mesial-distal direction 115 with respect to a specific tooth has been schematically indicated in FIG. 1. In addition, the lingual-labial direction 135 may be indicated with respect to the same tooth. In this figure, the third molars (wisdom molars) have been included.

Figure 2A:
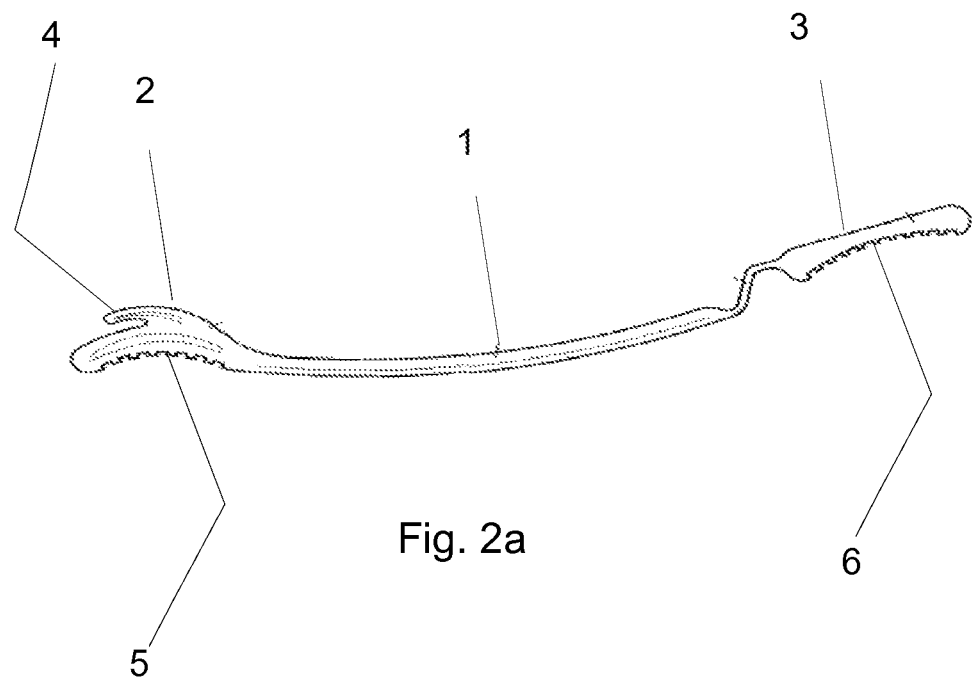
FIG. 2a-2b illustrate orthodontic devices according to some examples.
Figure 2B:
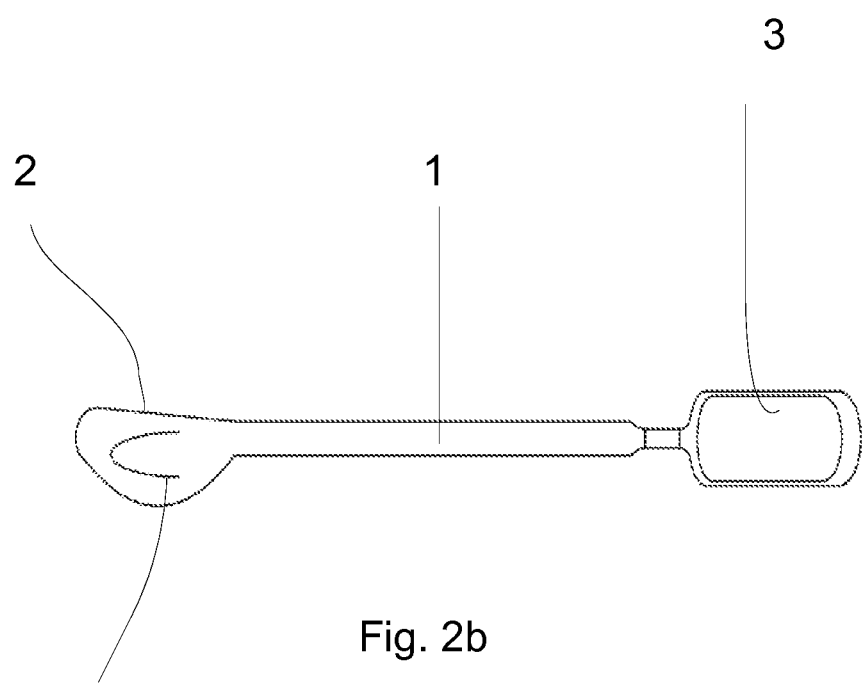

FIGS. 2a and 2b illustrate an orthodontic device that may be adapted for the segmental distalization of a premolar and a molar.

An elongated central bar (or "arm") 1 may be integrally formed with a distal part 3 that may include a distal base surface 6 adapted to be attached to a lingual surface of a molar (not shown in this figure). The elongated central arm 1 may also be integrally formed with a mesial part 2 comprising a mesial base surface 5 adapted to be attached to a lingual surface of a premolar (not shown). The elongated central bar, the distal part and the mesial part may thus form a monolithic element.

The base surfaces of both the distal part and the mesial part may comprise a shape suitable for retention. Although in the illustrated example a plurality of protuberances may be shown, other alternatives may be used. The base surfaces may be mounted on the teeth using e.g. adhesive dental cement.

The elongated central arm 1 may be substantially shaped following the lingual side of a plurality of teeth between the molar and the premolar of a patient. The central arm 1 may be slightly concave as shown in FIG. 2a.

A hooking element 4 may be located on the outer part of the mesial part 2. The hooking element 4 may be made of the same material and may be integrally formed with the mesial part 2. The hooking element 4 may however have any suitable shape and be made of any suitable material as long as an actuating element can be retained.

An elastic element (not shown) e.g. a rubber band may be strung around the hooking element 4 and the elastic element may provide a mesial-distal force (backwards) in the premolar. To this end, a second end of such an elastic element may be attached to e.g. a hook on a bracket or an implant. The elastic element can thus actuate on the orthodontic device and provide a force in a distal direction.

Furthermore, due to the elongated central arm 1 connecting the distal base surface 6 and the mesial base surface 5 plus the elastic element, a molar (not shown in this figure) may be pushed backwards. A set of teeth including the premolar and the molar and the teeth in between may thus be repositioned as a group. At the same time, due to the position of the distal base surface 6 onto a molar, a rotation in the distal direction of a molar ("uprighting") may be achieved.

The hooking element in FIG. 2b may be seen to extend forwards (i.e. in a mesial direction). The hooking element may extend forwards in a substantially straight manner and may be provided in a substantially central portion of the mesial part. The symmetric shape of the resulting orthodontic device makes it possible for a single device to be fitted both in a right and a left quadrant of a patient's mouth. The hooking element may in alternative examples also extend slightly upwards for improved retention.

In some (non-illustrated) examples, the hooking element may be in the form of a round or substantially mushroom-shaped button around which an elastic band can be fitted.

The orthodontic device may be made from any suitable material including e.g. metals (alloys) or polymer: the polymers may be fibre-reinforced or not. In addition, the orthodontic device may also be manufactured with materials that can include translucent or transparent material, and thus the aesthetic aspects may be improved. The orthodontic device may be manufactured in different ways. This device may be moulded. When it is made from metals, they may also be made by machining.

Figure 3A:
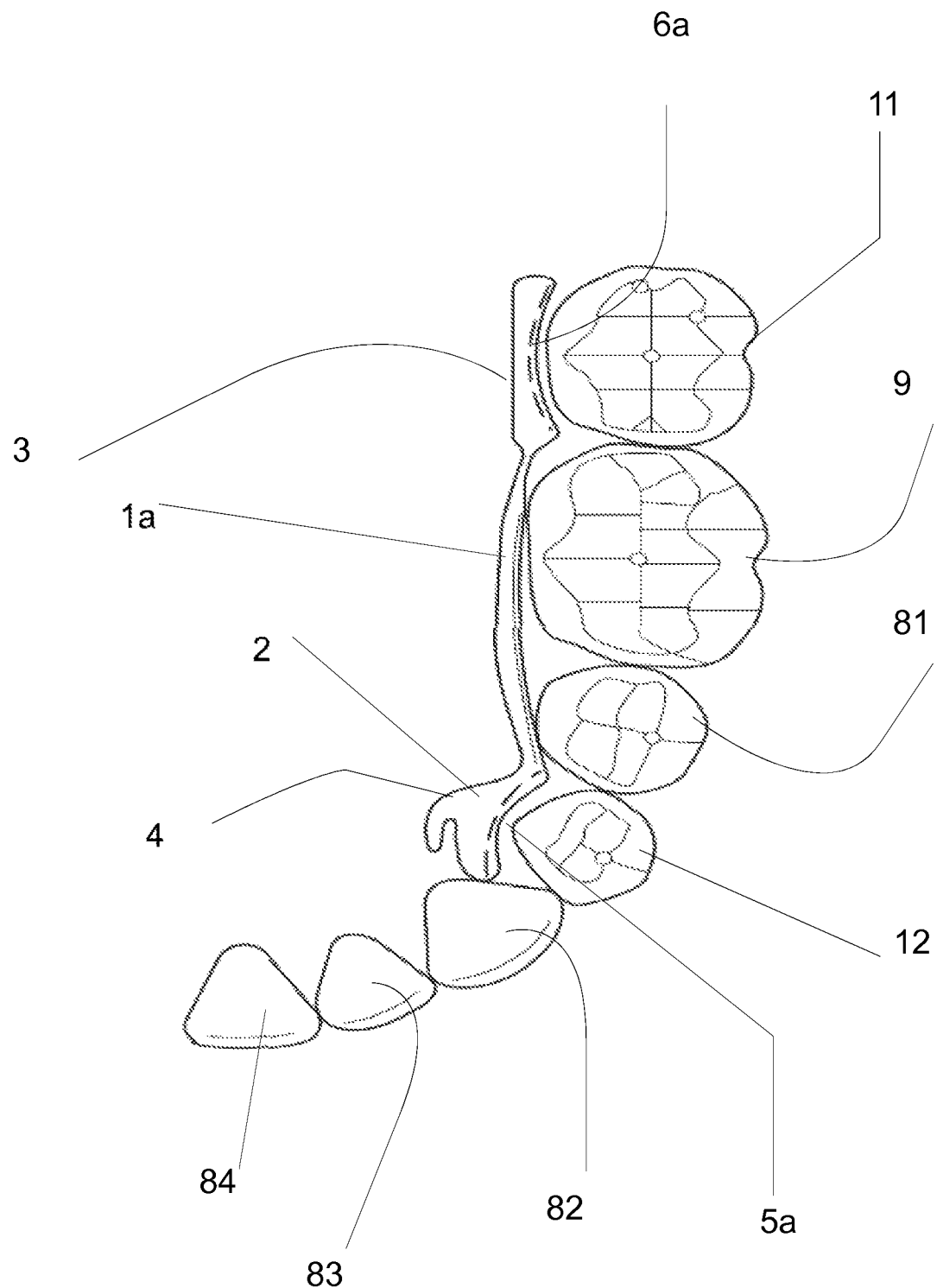
FIG. 3a-3b schematically illustrate various examples of the present invention in the lower left quadrant of the mandible (lower jaw bone)

FIG. 3a illustrates an orthodontic device adapted for the segmental distalization of the first premolar 12 and a second molar 11 located in the left quadrant of the mandible (lower jaw bone).

In this figure, the tooth 11 may be regarded to as the mandibular second molar 11. Further indicated are the first molar 9, the second premolar 81, the first premolar 12, a canine 82, and incisors 83 and 84.

The distal base surface 6a of the device may be attached to a lingual surface of the second molar 11. The mesial base surface 5a may be attached to a lingual surface of the first premolar 12.

The elongated central arm 1a may be substantially shaped to follow the lingual side of a second premolar and a first molar between the second molar and the first premolar both located in the mandible (lower jaw bone).

The attachment of the distal base surface 6a and/or the attachment of the mesial base surface 5a may be performed by means of a material suitable for retention e.g. adhesive dental cement; the adhesive dental cement may be placed onto the distal base surface 6a and/or the mesial base surface 5a. The mesial base surface 5a may be placed in a precise position onto the first premolar and/or the distal base surface 6a may be placed in a precise position onto the second molar, the excess of adhesive dental cement may be removed, thus the distal base surface 6a and the mesial base 5a surface may be fixed. Some other elements for the attachment may also be possible.

In preferred examples, the dimensions of the device are such that practitioners only have to fit the device in a position where they would usually mount a bracket. This can make the device particularly easy to use for practitioners and may lead to higher acceptance in the dental community. However, the exact position of the base surface with respect to a tooth may depend on a specific malocclusion and may thus be varied. In some examples of treatments, a professional may intentionally choose e.g. a relative forward portion of a molar for the attachment of the orthodontic device. If a (pushing) force is provided in a diagonal direction (i.e. having both a component in a rearward direction and a component substantially sideways and thus perpendicular to the rearward direction), then a suitable rotational moment may be provided to the molar to add a rotation around its roots.

When an actuating element such as e.g a rubber band is fitted around hooking element 4 at a first end of the actuating element and around another retention element at a second end of the actuating element, a backwards force is provided to the set of teeth involving, the first and second premolars and the first and second molars. The whole block of teeth may thus be moved backwards. The second retention element may e.g. be a hook on an implant or on a lingual bracket.

In the case of the distalizing device being mounted in the mandible, a bracket comprising such a hook may be mounted on a maxillary molar, e.g. a maxillary first molar. A maxillary ferrule may ensure that the maxillary teeth do not move forward under the influence of the reaction force acting of the bracket.

Figure 3B:
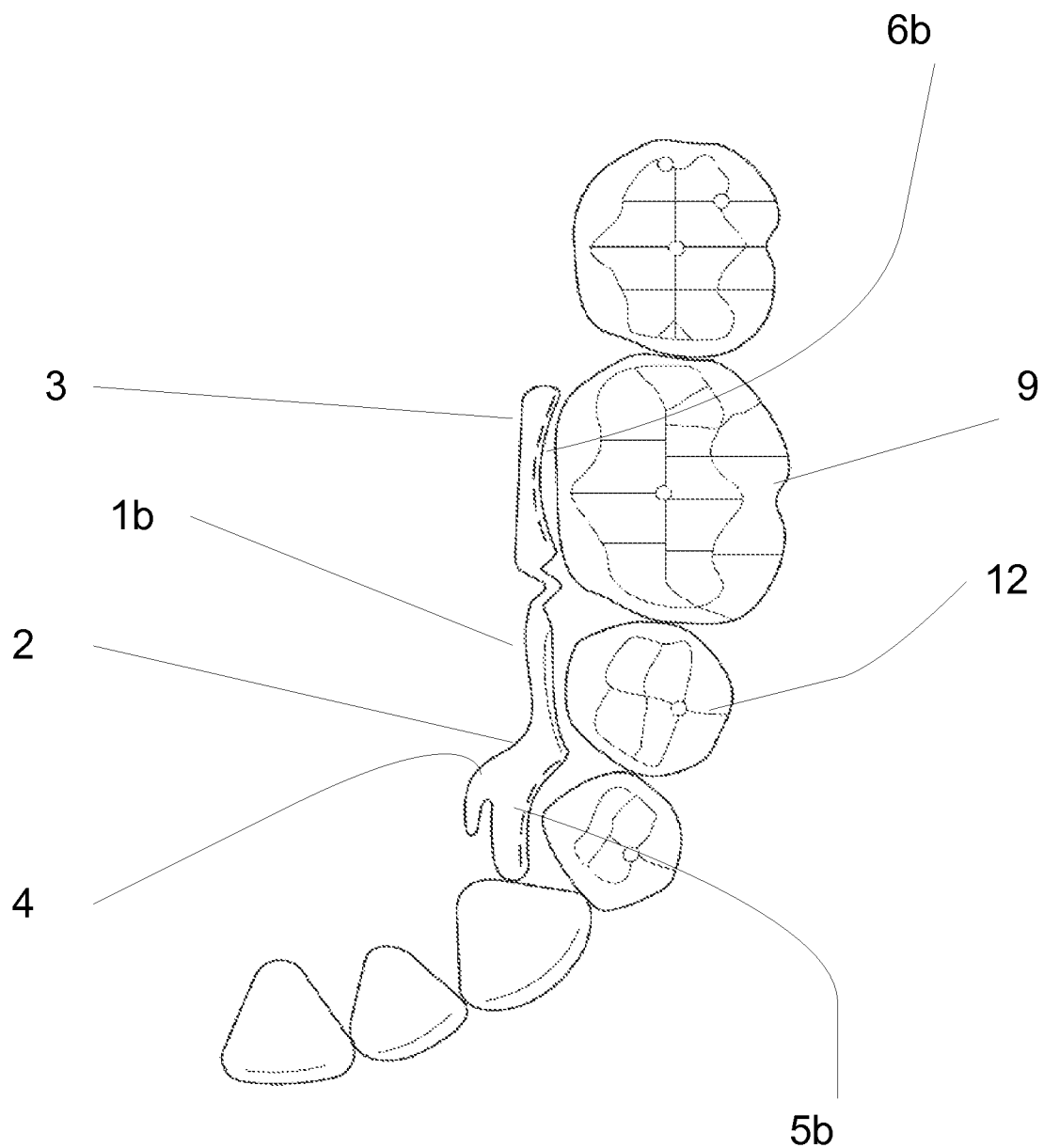

FIG. 3b illustrates an orthodontic device adapted for the segmental distalization of the first premolar 12 and a first molar 9 located in the left quadrant of the mandible (lower jaw bone). In this figure same reference numbers denote the same elements as those in the FIG. 2a. The distal base surface 6b may be attached to the lingual surface of the first molar 9. The mesial base surface 5b may be attached to the lingual surface of the first premolar 12.

The elongated central arm 1b may be substantially shaped following the lingual side of a second premolar between the first molar 9 and the first premolar 12 both located in the mandible (lower jaw bone). The attachment of the distal base surface 6b and/or the attachment of the mesial base surface 5b may be performed in substantially the same way as described in FIG. 2a.

Furthermore, the central arm 1b may be curved outwards (in the labial direction) following the gap between the second premolar 81 and the first molar 9 at the lingual side and inwards (in the lingual direction) near the distal base surface 6b.

Figure 3C:
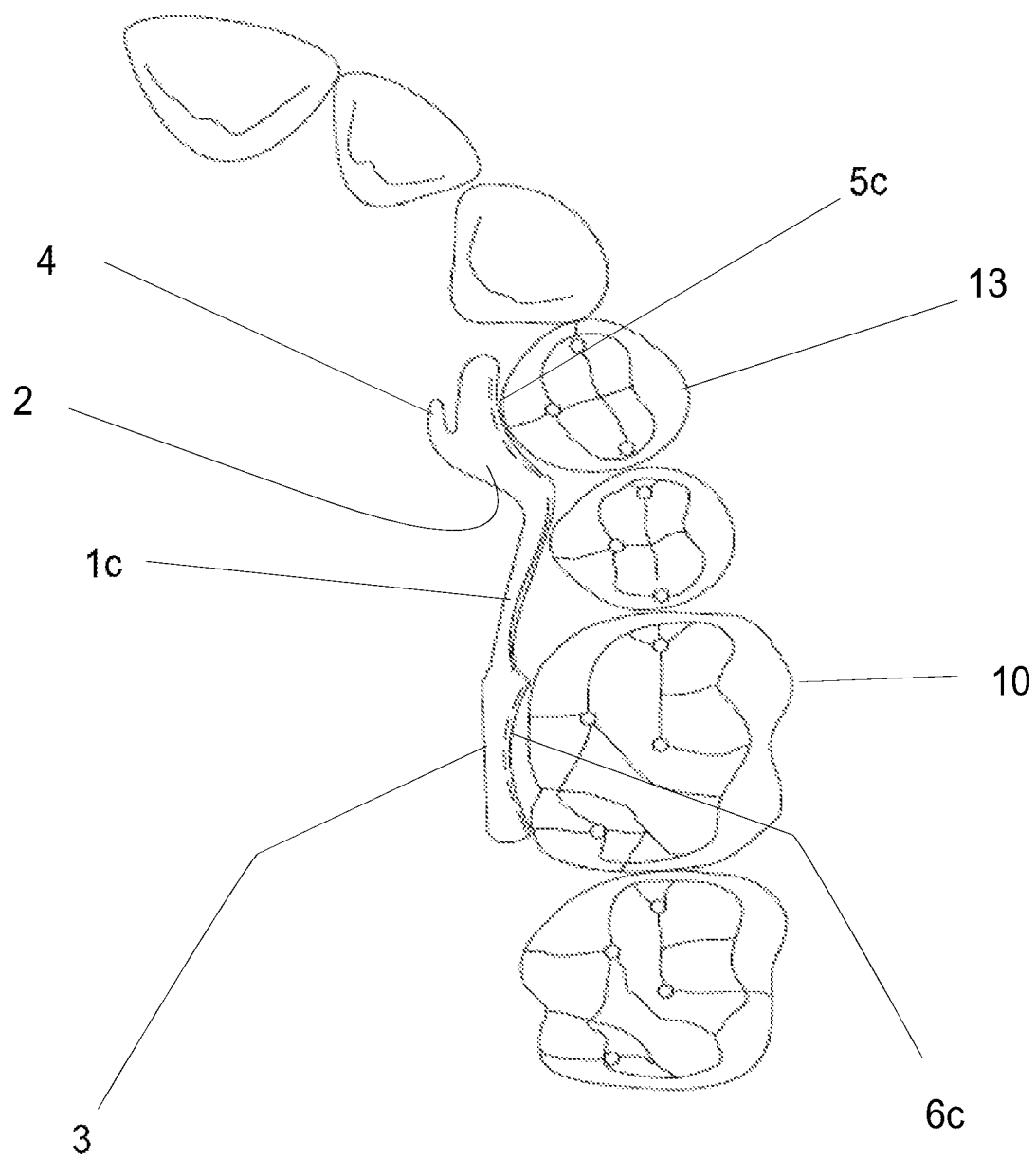
FIG. 3c-3f schematically illustrate various examples of the present invention in the upper left quadrant of the maxilla (upper jaw bone)
Figure 3D:
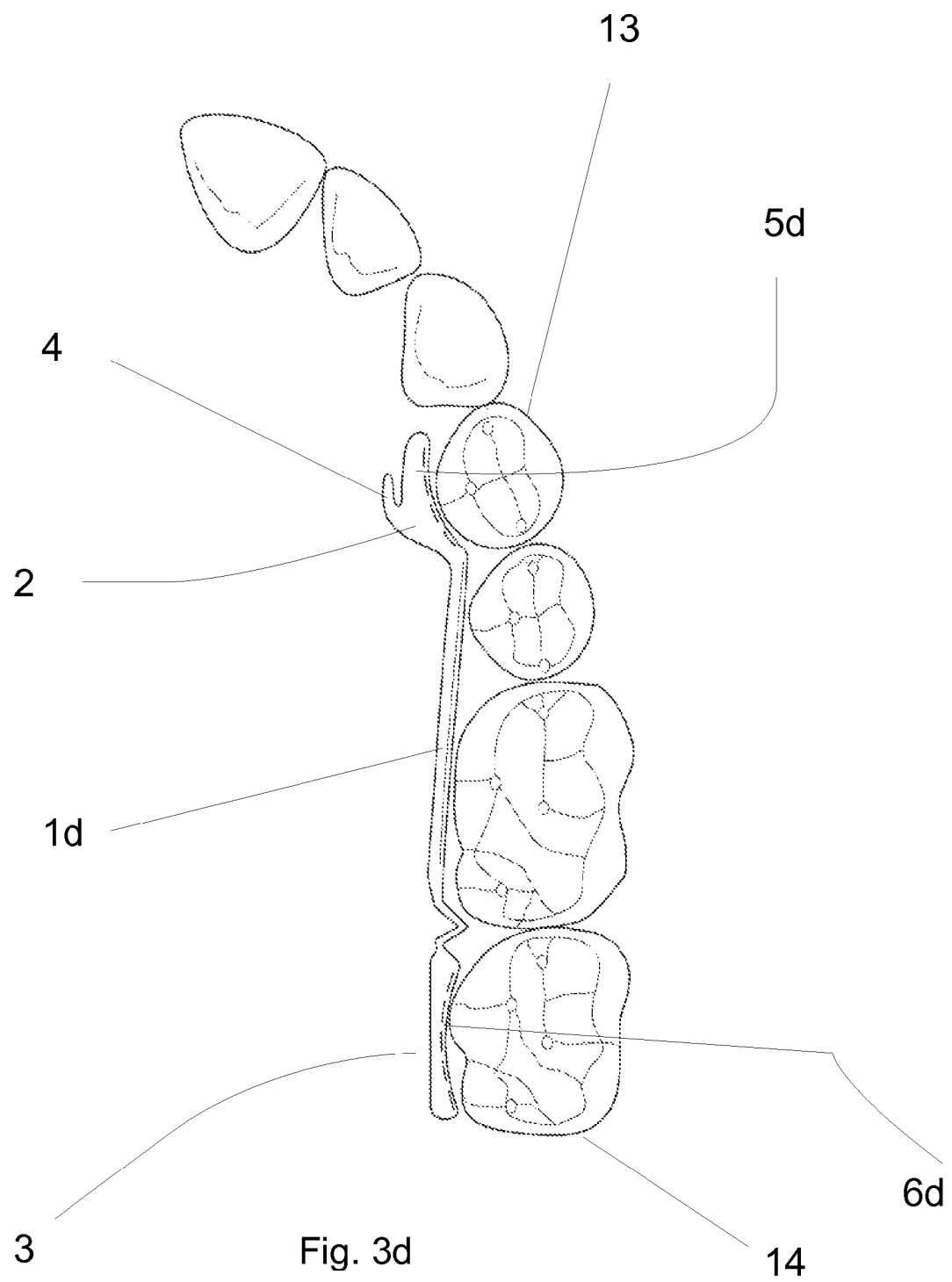

The FIGS. 3c and 3d show similar examples for maxillary distalization. Also here, the distalization device may be attached to either a first or second molar. In these figures same references numbers denote the same elements as those in the FIG. 2a. An implant with a retention element may be provided in the patient's palate. A rubber band or other elastic element may be connected between such an implant and the hooking element 4. Alternatively, a bracket mounted on a lingual surface of a mandibular tooth may serve for the necessary retention and backwards traction. In particular, a bracket may be mounted on a mandibular molar, in particular a first molar. Similarly as before, a ferrule may be provided for the mandibular so that the mandibular teeth do not move forward.

Figure 3E:
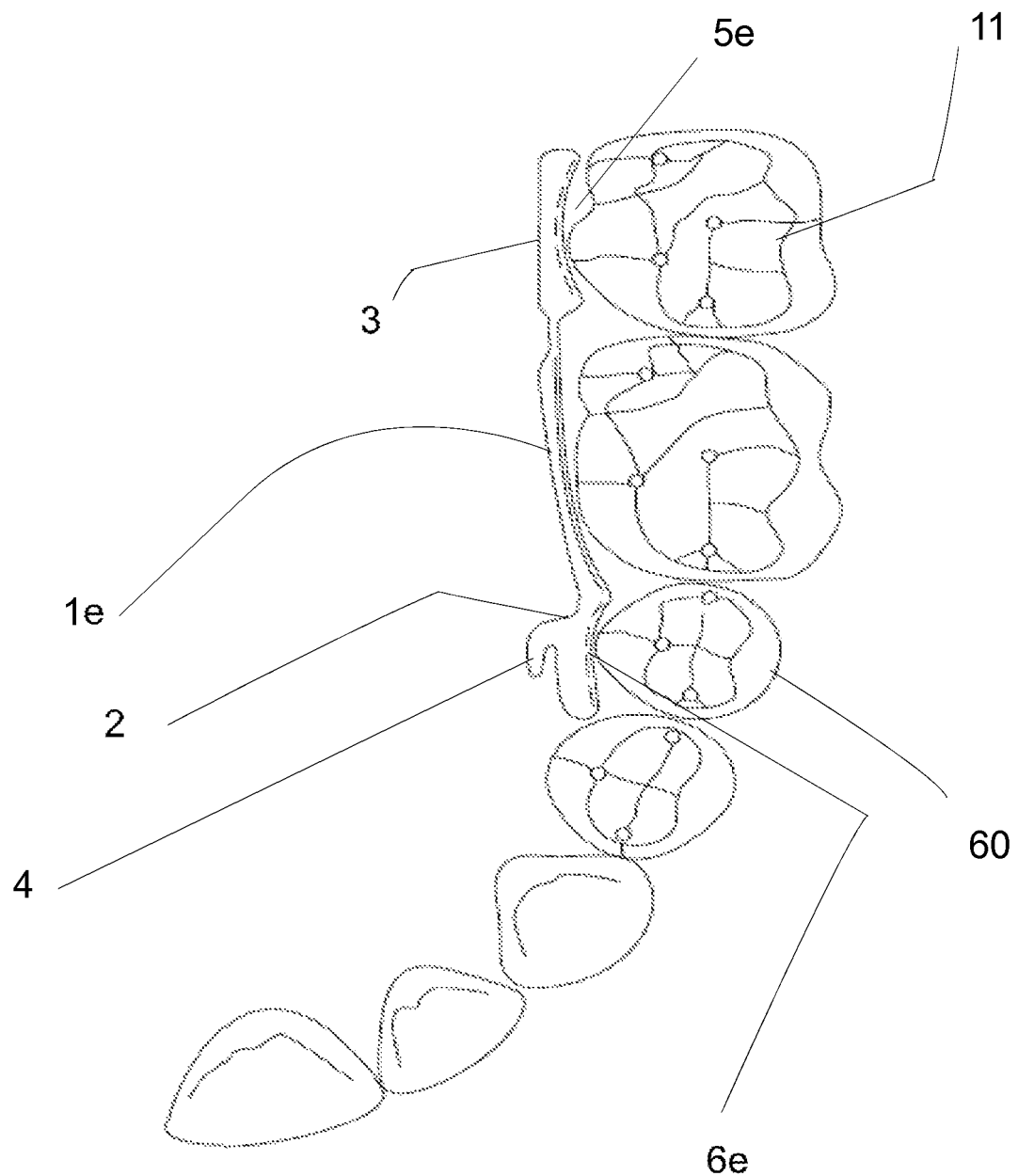

FIG. 3e shows further similar examples for maxillary distalization. In this particular example, an orthodontic device adapted for the segmental distalization of the second premolar 60 and a second molar 11 located in the left quadrant of the mandible (lower jaw bone) may be provided. In this figure same references numbers denote the same elements as those in the FIG. 2a.

In other non-illustrated examples, the distalizing device may connect a premolar to a third molar ("wisdom tooth").

Figure 3F:
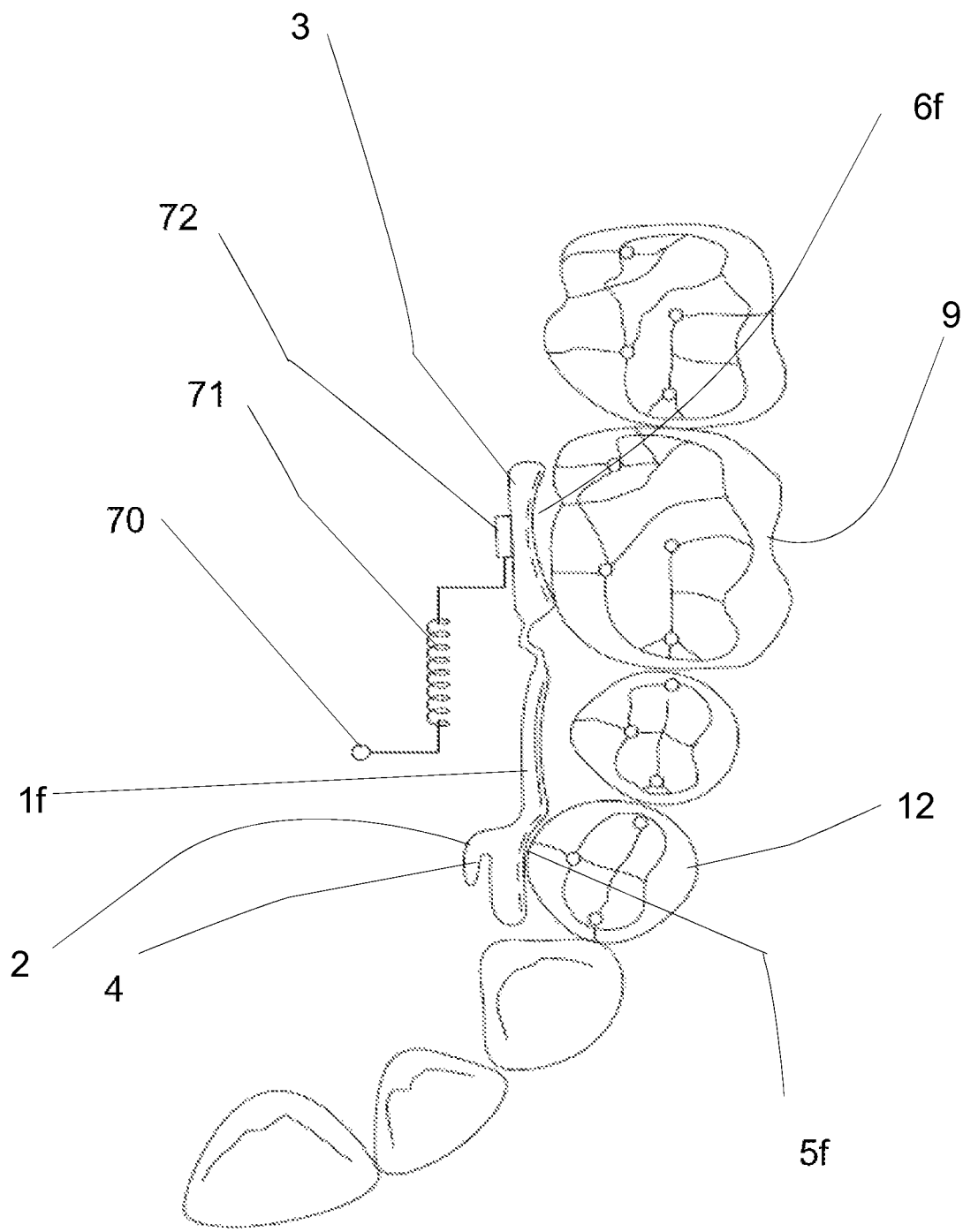

The FIG. 3f illustrates an orthodontic device adapted for the segmental distalization of the first premolar 12 and a first molar 9 located in the left quadrant of the maxilla (upper jaw bone).

The distal base surface 6f may be attached to a lingual surface of the second molar 9. The mesial base surface 5f may be attached to a lingual surface of the first premolar 12. The elongated central arm 1f may be substantially shaped following the lingual side of a first premolar 12 and a first molar 9 both located in the mandible (lower jaw bone). The attachment of the distal base surface 6f and/or the attachment of the mesial base surface 5f may be performed in a similar way as described in FIG. 3a.

A retention element 72 may be provided on the distal part 3 of the elongated central arm 1. The retention element 72 may be made of the same material and integrally formed with the distal part 3. The retention element may be in the shape of a pocket receiving a first end of the actuating element 71.

The actuating element 71 may be a resilient element 71 such as e.g. a spring The resilient element 71 may be made of metal but other materials are also possible, An implant pin 70 may be attached in the palate. The mesial end of the resilient element 71 may be attached to the pin connection 70. In further examples, the actuating element pushing backwards against the molar may comprise a spring actuated piston.

In this way, the resilient element may provide a force in the distal part 3 of the distalizer backwards (mesial—distal direction) and therefore, extra rearwards force in the first molar 9 may be provided. In some examples, a pulling arrangement (involving e.g. a hooking element with an elastic band) may be combined with a pushing arrangement (involving e.g. a receptacle on a distal part).

In an alternative arrangement, a base surface of the distal part of the orthodontic device may be mounted in a relatively forward position on the molar. If a (pushing) force is provided in a more diagonal direction, then the component of the force in the sideways (lingual-labial) direction may establish a rotational moment to the molar to aid in a rotation around its roots.

Consequently, in the hereinbefore illustrated examples, the amount of space available for the teeth may be increased. In many treatments, this is an alternative to tooth extraction.

Figure 4:
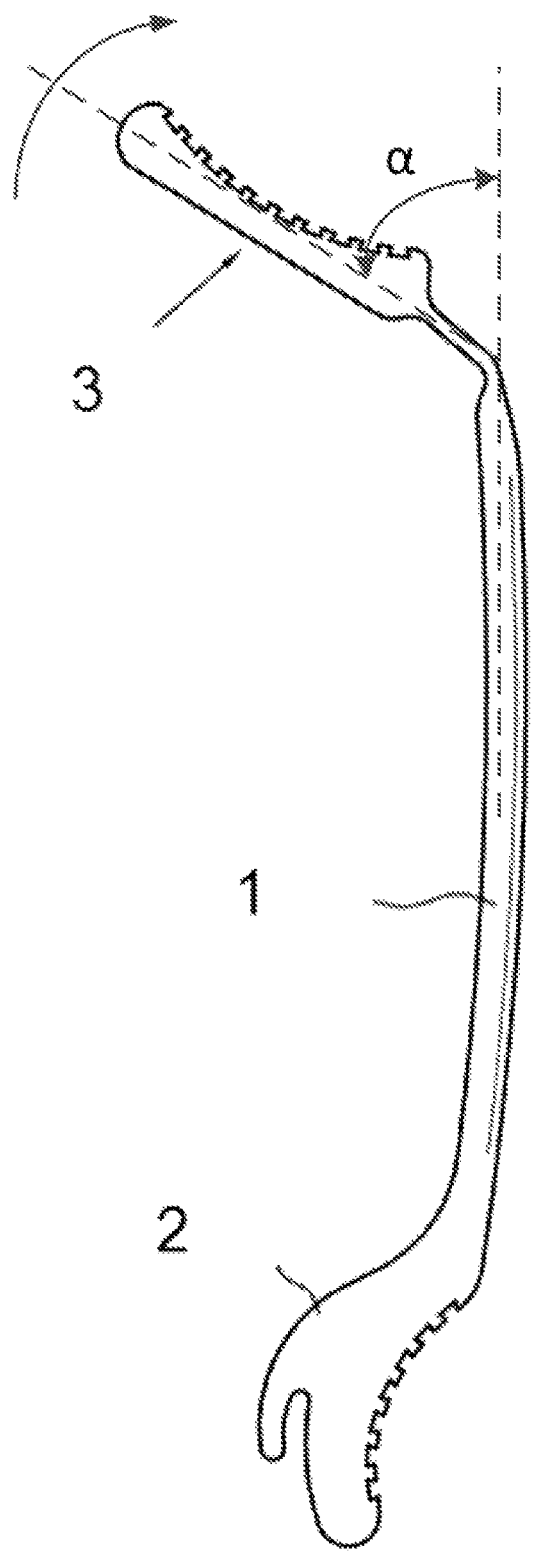
FIG. 4 illustrates a distalizer according to a further example.

FIG. 4 illustrates another example of an orthodontic device adapted for the segmental distalization. The distal part 3 of the elongated central arm 1 may be elastically deformable such that an angle between the distal part 3 and the elongated central arm 1 may be adapted. The flexibility may be provided by a distal end region of the central arm being thinner than other portions of the central arm. The distal part may thus have a relatively wide range of movement with respect to the central arm.

In its default or "natural" state, i.e. before deformation, the angle α between the longitudinal axis of the elongated central arm and the base surface may be between 90° and 30°, and in particular between 75° and 45°.

Consequently, the orthodontic device may be elastically deformed in the distal part. Due to this deformation the orthodontic device may be installed with an initial tension, and thus an extra force may be exerted on a molar.

Similarly, in some other examples, such flexibility (involving a thin portion of a region of the central arm) could also be provided for the mesial part. Elastic deformation of the mesial portion may thus achieve additional inwards force to the first premolar (not shown) in a lingual direction.

In some examples, both the mesial part and the distal part may have sufficient flexibility and may be elastically deformed before mounting.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. An orthodontic device for segmental distalization of a set of teeth in a mouth of a patient, wherein the teeth have a labial side facing outwards, and a lingual side facing inwards, the device comprising:
   an elongated central arm;
   a distal part comprising a distal base surface adapted to be attached to a lingual surface of a molar, wherein the distal part is located at a distal end of the elongated central arm;
   a mesial part comprising a mesial base surface adapted to be attached to a lingual surface of a premolar, wherein the mesial part is located at a mesial end of the elongated central arm,
   wherein the mesial part and/or the distal part comprises a first retention element for retention of a first end of an external actuating element, and
   wherein the elongated central arm extends between the mesial base surface and the distal base surface and is shaped to substantially follow the lingual side of the set of teeth, and
   wherein the elongated central arm is not connected to any other tooth.

2. The device according to claim 1, wherein the orthodontic device is configured to be attached to a first molar and a first premolar.

3. The device according to claim 1, wherein the orthodontic device is configured to be attached to a second molar and a first premolar.

4. The device according to claim 1, wherein the orthodontic device is configured to be attached to a second molar and a second premolar.

5. The device according to claim 1, wherein the orthodontic device is configured to be positioned in the mandible of the patient.

6. The device according to claim 1, wherein the orthodontic device is configured to be positioned in the maxilla of the patient.

7. The device according to claim 1, wherein a distal end region of the elongated central arm is provided with flexibility such that an angle between the distal end region of the elongated central arm and a neighboring portion of the elongated central arm can be adapted to the patient's teeth.

8. The device according to claim 7, wherein in an undeformed state, an angle α between a longitudinal axis of the elongated central arm and the distal base surface is between 30° and 90°.

9. The device according to claim 8, wherein in the undeformed state, the angle α between the longitudinal axis of the elongated central arm and the distal base surface is between 45° and 75°.

10. A device according to claim 7, wherein the distal end region is thinner than the neighboring portion of the elongated central arm.

11. A device according to claim 1, wherein the mesial part first retention element comprises a hooking element for retention of a first end of an elastic element, wherein the elastic element is a rubber band.

12. The device according to claim 1, wherein the elongated central arm is curved and has a concave side facing towards an inside of the mouth.

13. The device according to claim 1, wherein the elongated central arm is substantially straight.

* * * * *